United States Patent [19]

Wilmott

[11] Patent Number: 5,509,416
[45] Date of Patent: Apr. 23, 1996

[54] FETAL HEART DETECTOR

[75] Inventor: Barnaby Wilmott, West Sussex, Great Britain

[73] Assignee: Oxford Medical Limited, Witney, Great Britain

[21] Appl. No.: 335,465

[22] Filed: Nov. 7, 1994

[30]  Foreign Application Priority Data

Nov. 8, 1993 [GB] United Kingdom ............... 9322977

[51] Int. Cl.⁶ ........................................ A61B 8/00
[52] U.S. Cl. ........................................ 128/661.07
[58] Field of Search ........................ 128/660.1, 661.07, 128/661.08, 661.09, 662.1, 662.01, 662.03, 662.04; 73/861.25

[56]         References Cited

U.S. PATENT DOCUMENTS

| | | | |
|---|---|---|---|
| 3,780,725 | 12/1973 | Goldberg | 128/662.04 |
| 4,226,229 | 10/1980 | Eckhart et al. | |
| 4,986,276 | 1/1991 | Wright | 128/662.04 |
| 5,309,915 | 5/1994 | Ember | 128/661.07 |

FOREIGN PATENT DOCUMENTS

| | | |
|---|---|---|
| 0307258 | 3/1989 | European Pat. Off. . |
| 0359839 | 3/1990 | European Pat. Off. . |
| 2808755 | 9/1979 | Germany . |
| WO8303750 | 11/1983 | WIPO . |
| WO8702878 | 5/1987 | WIPO . |

*Primary Examiner*—George Manuel
*Attorney, Agent, or Firm*—Hoffmann & Baron

[57]          ABSTRACT

A self contained hand held fetal detector comprises an ultrasonic receiver and transmitter (23). Selectively actuable ultrasonic receiving and transmitting circuits (25,21) are connected to the ultrasonic receiver and transmitter (23) with a controller (24) for actuating either the ultrasonic receiving circuit (25) or the ultrasonic transmitting circuit and a loudspeaker (29) connected to the ultrasonic receiving circuit (25) for generating an audio output signal. The detector comprises a single unit (13) and the controller (24) modifies at least one of the transmitted and received signals, to prevent interference in the received ultrasound.

5 Claims, 4 Drawing Sheets

FETAL HEART DETECTOR

FIELD OF THE INVENTION

This invention relates to a fetal heart detector, in particular to a hand held detector.

DESCRIPTION OF THE PRIOR ART

Conventional fetal heart detectors include hand held, audible detectors which are formed in two parts connected via cabling. The first part is an ultrasonic probe having two angled ultrasonic crystals, one for transmission and one for reception. An ultrasonic signal is continuously transmitted typically at a frequency of 2 MHz and this causes reflections from surfaces in the medium through which it passes. The receiving crystal continuously senses reflected signals.

If an object, off which the signals are reflected, moves this causes a doppler shift in the frequency which is detected. This doppler shift is typically in the audio range when caused by movement of a fetal heart wall and the signal can be amplified and output directly through an audio loudspeaker in the second part. The main advantage of an audio output to a pocket monitor is that it enables the mother to hear the fetal heartbeat, thus reassuring the mother. Additionally in view of its focused ultrasonic beam it allows earlier detection of the fetal heart beat than a bedside monitor where a larger transducer having a divergent beam is used.

A hand held detector may be used by a mid-wife in the home or in a hospital, or by consultants to give the heart rate of the fetus. The heart rate may be displayed directly on the monitor.

It is desirable that the cost of manufacture of such detectors should be kept as low as possible and that they should be easy to use and to carry. Conventional hand held detectors rely on continuous wave transmissions of ultrasonic signals. A continuous wave system has no limit on the distance of travel of a wave before its reflected wave can be detected in the receiving crystal. This means that movement of the loudspeaker in the output section will be detected by the receiving crystal unless there is some form of separation between the transducer and the output section. Typically, this is achieved by housing the transducer in a probe and using a separate audio unit connected to the probe by means of a cable.

Other proposed solutions to this problem include providing the probe with a transmitter to transmit information via telemetry to a completely separate audio unit such as described in EP-A-0367251, or using infrared transmission. An alternative is to use headphones rather than a loudspeaker but this does not overcome the disadvantages inherent in two piece units which require additional connectors and separate manufacturing of the parts. The inclusion of connectors and cables automatically provides an undesirable level of unreliability and cost. Testing the complete unit requires the separately manufactured parts to be put together adding to the cost.

SUMMARY OF THE INVENTION

In accordance with the present invention, a self contained hand held fetal detector comprises ultrasonic receiving and transmitting means; selectively actuable ultrasonic receiving and transmitting circuits connected to the ultrasonic receiving and transmitting means; control means for actuating either the ultrasonic receiving circuit or the ultrasonic transmitting circuit; and a loudspeaker connected to the ultrasonic receiving circuit for generating an audio output signal, the detector comprising a single unit and the control means including means for modifying at least one of the transmitted and received signals, to prevent interference in the received ultrasound.

Preferably, the modifying means comprises means for causing a pulsed signal to be transmitted.

The ultrasonic receiving circuit and ultrasonic transmitting circuit are actuated with a time delay, between the end of a transmission period and the start of a reception period, such that an area ahead of the transducer is provided in which everything reflected within that distance is not detected by the receiving circuit thereby cutting out near field interference and feedback due to the reflections affected by moving parts of the loudspeaker. This allows a single piece monitor to be manufactured.

However, at high gain settings, an additional form of unwanted feedback can occur in the presence of strong reflections from large stationary objects within the depth range of the gated ultrasound signal. Vibrations from the loudspeaker once initiated by any means, will be mechanically coupled to the ultrasound transducer causing it to move microscopically relative to objects within its ultrasonic field. Such movements will cause reflections from stationary objects to be Doppler shifted and appear as audio on the loudspeaker. The process is then repeated resulting in an audio "positive feedback" tone when there should be no signal present.

Preferably, the detector further comprises shift means to shift the frequency or phase of the audio signal by a non-integer multiple of the audio-frequency.

Thus recirculating signals due to reflections within the depth range of the ultrasonic circuit, such as large organs of the mother, do not reinforce one another.

A device which can fulfil this function is a "pitch shifter" which can be inserted into the audio amplifier section of the circuit. Such devices produce an output signal which is a frequency shifted version of any audio signal presented to the input. In the present application the signals of interest are already the result of a frequency shift (the Doppler effect) so provided the signals remain in the audio bandwidth the effect of being shifted once by a few semitones is of little significance. However, by using the device to give a frequency shift which is a non-integer multiple of the input frequencies, the effect on potential feedback signals is to change their frequency and hence their phase each time they re-circulate through the system so they are unable to reinforce and are quickly shifted out of the audio bandwidth preventing unwanted tones.

Preferably, the audio signal is full wave rectified. This allows a smaller loudspeaker to be used.

Preferably, the detector further comprises display means to display a digital output relating to a frequency of a signal received by the ultrasonic receiving circuit. For example, a digital output of the heart rate, may be displayed at the same time as the audio output, for the benefit of the midwife or consultant using the monitor.

Preferably, the detector further comprises a sealed housing and wherein the loudspeaker is covered by an impermeable membrane.

The seal and membrane are waterproof and dustproof, making cleaning easier and allowing the detector to be used during water births.

BRIEF DESCRIPTION OF THE DRAWINGS

Some examples of apparatus in accordance with the present invention will now be described and contrasted with a known example with reference to the accompanying drawings, in which.

EMBODIMENT

Figure 1:
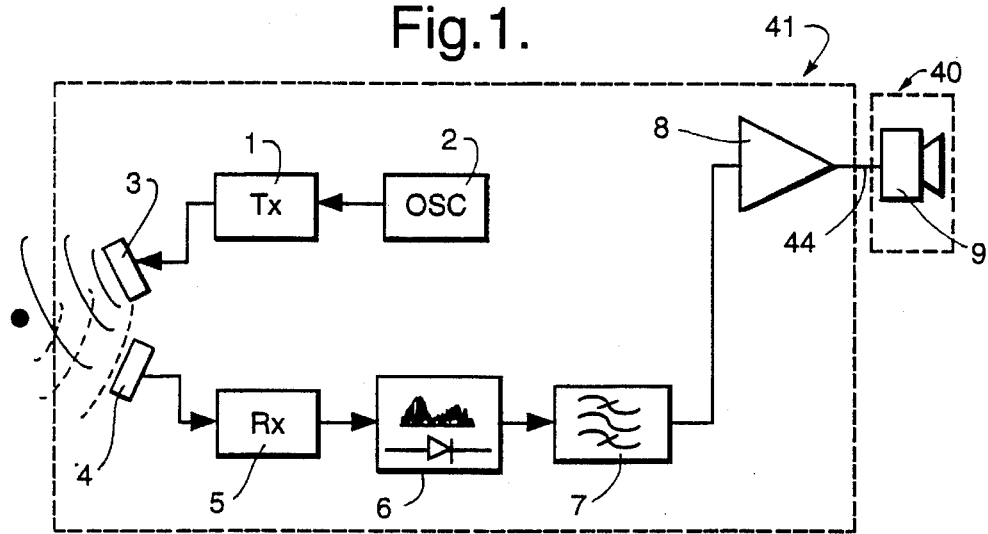
FIG. 1 shows a conventional monitoring unit.

In a conventional two piece system, such as that shown in FIG. 1, a loudspeaker 9 is housed 40 separately from a transducer circuit 41. In the circuit 41, a transmitter 1 is driven by an oscillator 2 to excite a transmitting crystal 3. The transmitting crystal is angled relative to a receiving crystal 4 such that when an ultrasonic signal emitted from the crystal 3 impinges on a moving object and is reflected back it is reflected towards the receiving crystal 4 with a differential frequency in the audio range. A signal received in receiver 5 is rectified 6 and filtered in a filter 7 to obtain the differential audio frequency output which is then amplified by an amplifier 8. The amplified signal is output to the loudspeaker 9 via a connection cable 44.

Figure 2:
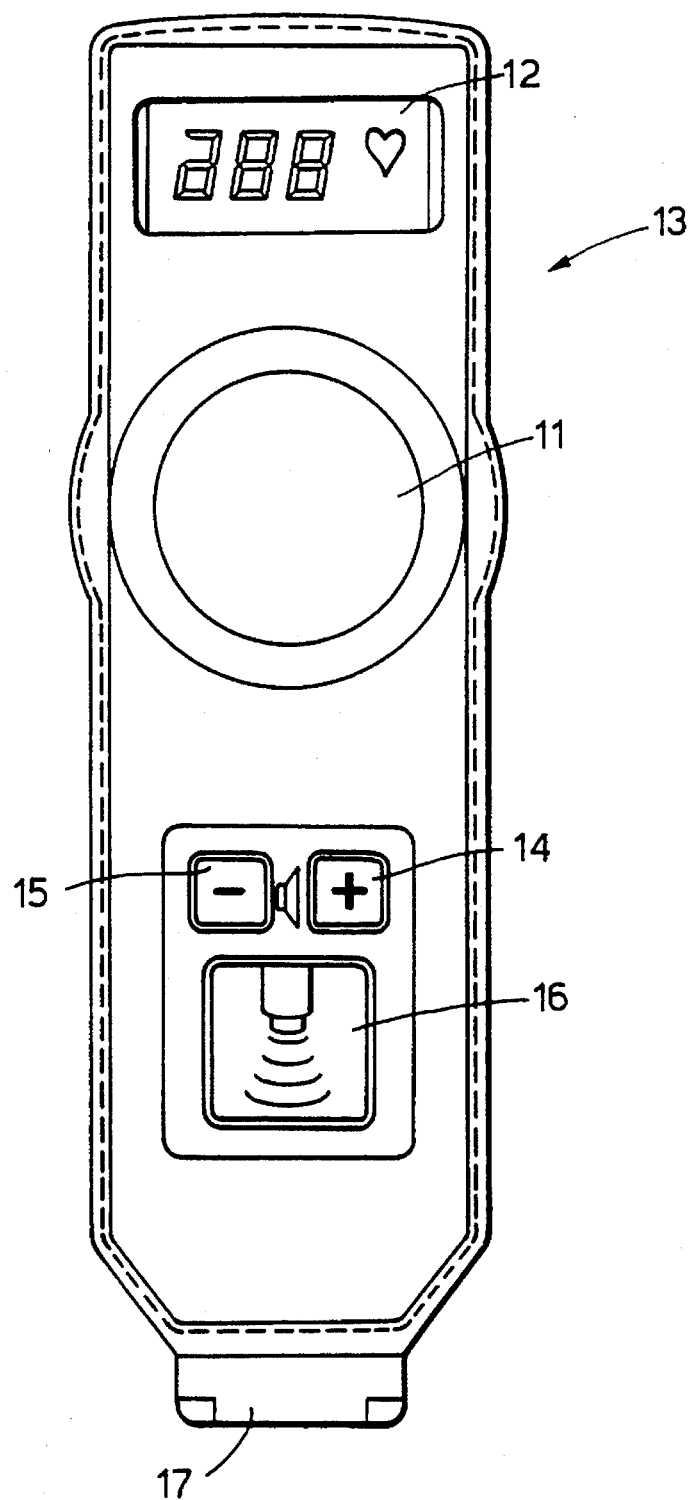
FIG. 2 is a perspective view of a monitor in accordance with the present invention.

In FIG. 2, a detector in accordance with the present invention is shown. A loudspeaker 11, control switches and digital display 12 are provided within a single body 13 which provides a waterproof cover, together with their associated circuitry (not shown). Operation of the detector is via the pair of control switches 14,15 for controlling the volume of the output and a single ON switch 16 for switching on the monitor. An ultrasonic transducer 17 is provided in one end of the body 13 of the monitor.

Figure 3:
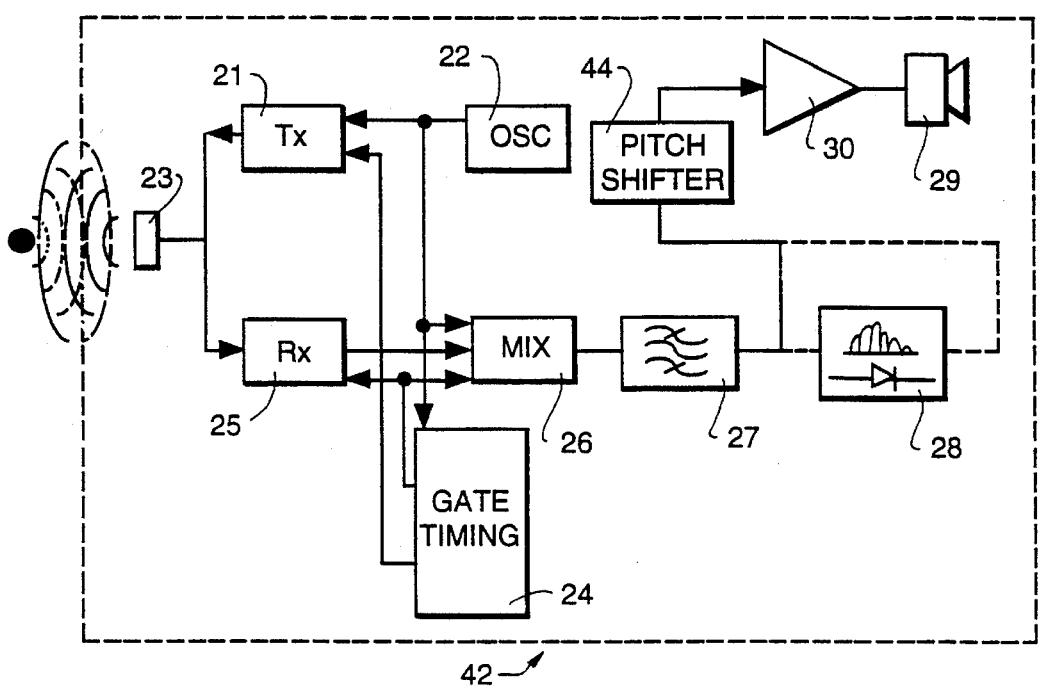
FIG. 3 is a block diagram of the circuit with the monitor.

FIG. 3 shows a block diagram of one example of the circuits mounted within the detector 13 of FIG. 2. A transmitter 21 is connected between an oscillator 22 and a single crystal 23. The oscillator also provides a signal to a gate timing circuit 24 and mixer 26. A receiver 25 is connected between the crystal and the mixer 26. Outputs of the gate timing circuit are connected to the mixer 26, receiver 25 and transmitter 21. An output from the mixer 26 is filtered in a set of filters 27, optionally full wave rectified in a rectifier 28 and pitch shifted in pitch shifter 44, then amplified by amplifier 30 and output through an audio loudspeaker 29. Automatic gain control is optionally applied to maximise audio performance and improve dynamic range. Only one of the transmitter 21 and receiver 25 operate at any one time. This timing is controlled by the gate timing circuit 24. A passive redirector directs any signal coming from the transmitter to the crystal, outward from the transmitter and any signal coming into the crystal, inward to the receiver.

The set of filters 27 removes the switching frequency between transmit and receive and a low frequency difference signal from the mixer 26, typically 100 hertz, is output to the pitch shifter 44 after filtering. The pitch shifter digitises the analogue signal, changes the sample rate by digital means and uses the samples to reproduce an analogue signal at the output. The output signal is similar to the input signal but with the frequencies shifted by a non-integer multiple. This signal is used to drive the loudspeaker through an audio amplifier 30. In this example, the rectifier 28 doubles the frequencies from the pitch shifter 44 in order that a small loudspeaker which does not work so well at very low frequencies, may be used. Typically, the ultrasonic frequency is of the order of 2 MHz.

Figure 4:
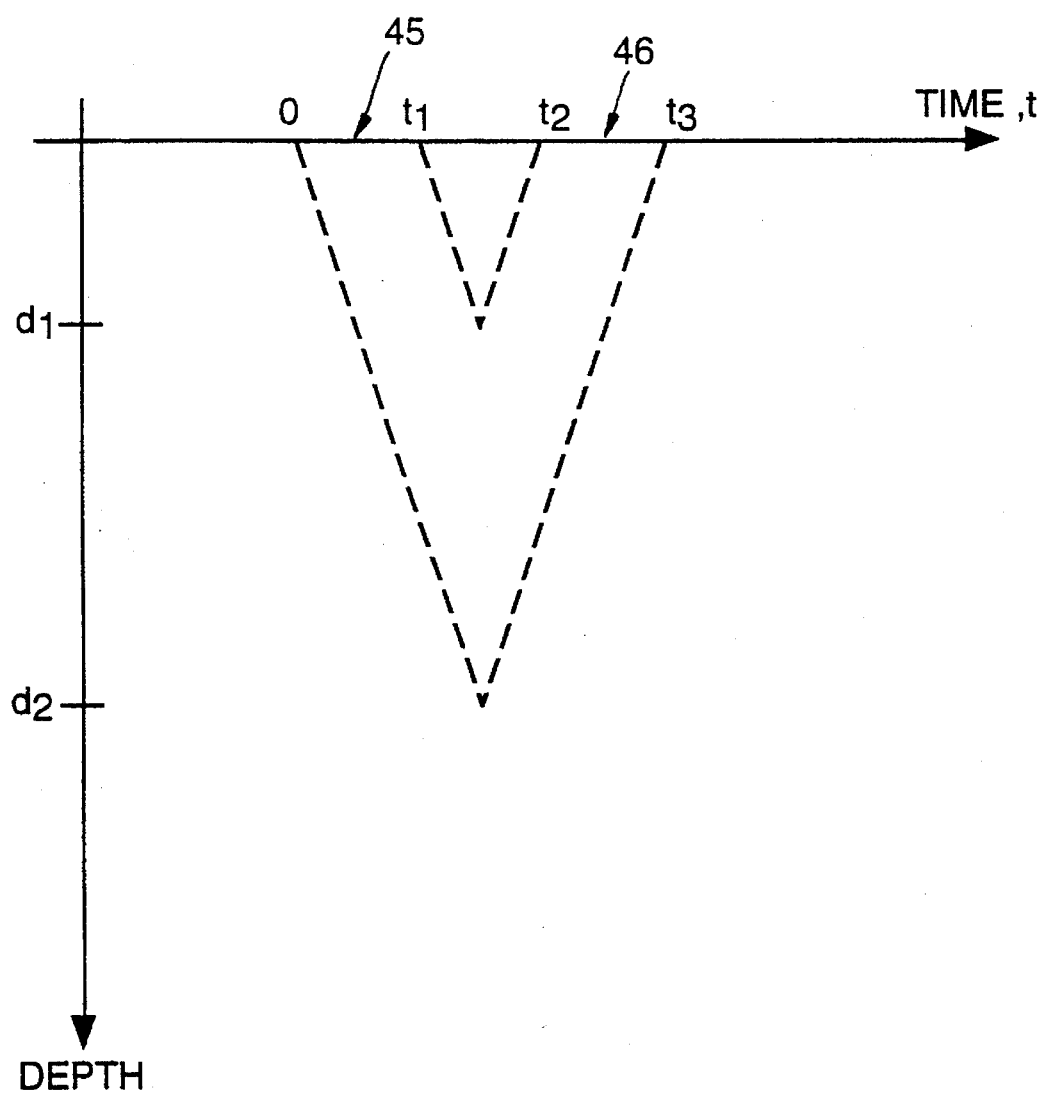
FIG. 4 illustrates how maximum and minimum depths for reflection are determined; and, FIG. 5 is a block diagram of a modified circuit for use with the monitor of FIG. 2.

The maximum depth of a reflected signal which can be detected is defined by the period for which a transmit pulse is transmitted $t_1$, a delay period $t_2-t_1$ and a receive period $t_3-t_2$ as illustrated in FIG. 4. For a fixed delay between the end of the transmit period and the start of the receive period the depth from which the leading part of the transmitted pulse may be reflected and still be detected at the trailing end of the receive period is the maximum depth for detection. The minimum depth which can be detected by the receiver 25 is determined by the delay period between the end of the transmit pulse and the start of the receive period. This avoids feedback due to movement of the loudspeaker being detected because it is within the dead zone resulting from delay between the end $t_1$ of the transmission period 45 and the start $t_2$ of the reception period 46.

Figure 5:
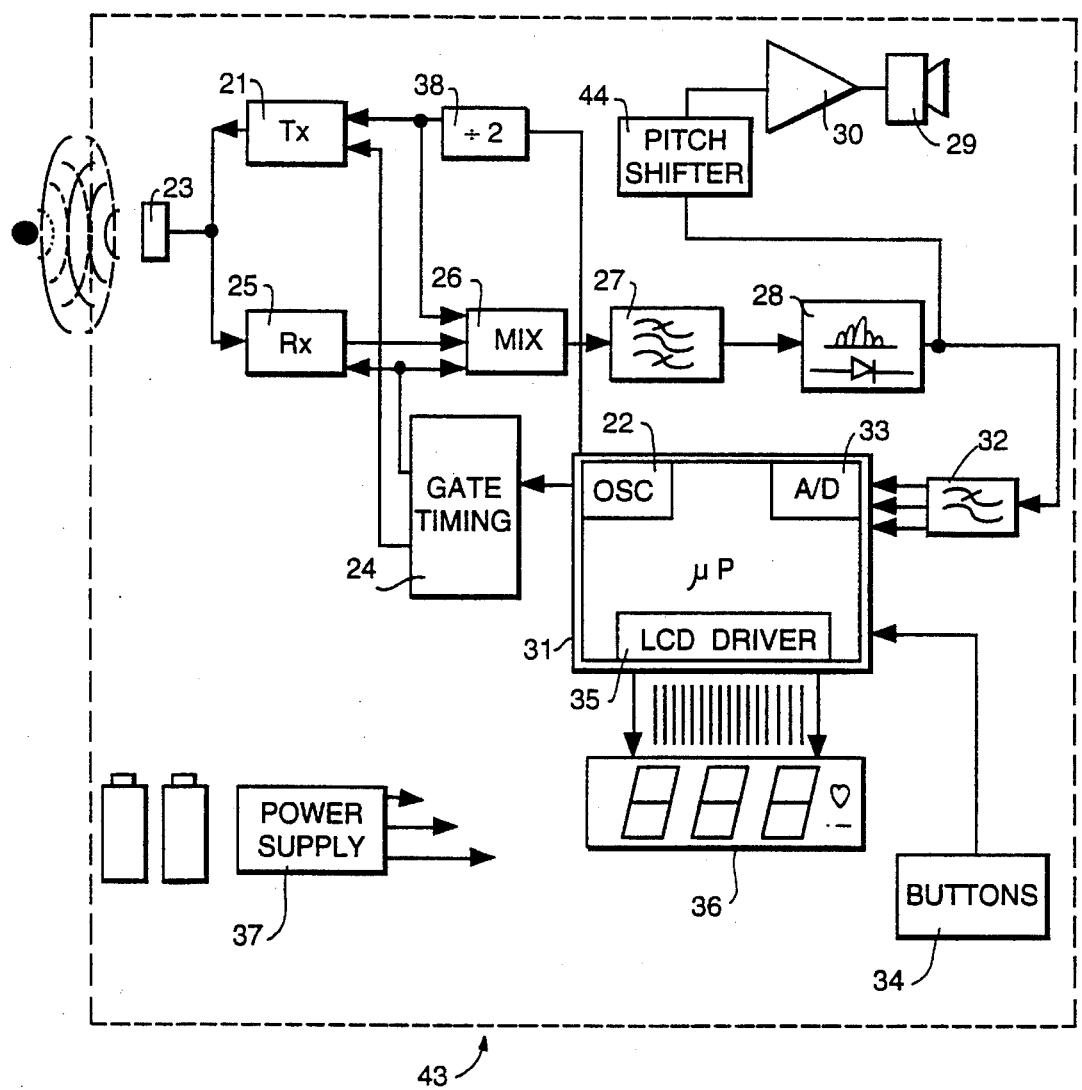

In another example of the present invention shown in FIG. 5, the oscillator 22 is incorporated in a microprocessor 31. The gate timing circuitry is divided between the microprocessor 31 and the gate timer 24 and a correct oscillation frequency is achieved by a divide by two circuit 38. The doubled frequency signal output from the full wave rectifier 28 is input to a low pass filter 32, then converted to a digital signal by the A/D converter 33. Within the processor 31 the digitized signal is matched with stored data patterns to obtain a value for the heart rate which is then output to the digital display 36 via a display driver 35. The processor may be controlled by the operator via buttons 34. A power source 37 connected to the processor 31 provides for the monitor to be self-contained.

If a single crystal is used, it has the advantages of ease of manufacture and cost reductions although two parallel crystals could equally be used, one connected to each of the transmit and receive circuits.

Typically, the volume and ON switches 14,15,16 will be membrane switches. Under processor control the monitor will automatically switch off a fixed time after displaying a value for the heart rate unless the ON switch is depressed again.

I claim:

1. A self contained, hand held, single unit fetal detector, the detector comprising ultrasonic receiving and transmitting means; a selectively actuable ultrasonic receiving circuit and a selectively actuable ultrasonic transmitting circuit, wherein each circuit is connected to the ultrasonic receiving and transmitting means; control means for actuating either the ultrasonic receiving circuit or the ultrasonic transmitting circuit; and a loudspeaker connected to said ultrasonic receiving circuit for generating an audio output signal, wherein the control means causes the ultrasonic transmitting circuit to transmit pulses of ultrasound and causes the ultrasonic receiving circuit only to pass signals to the loudspeaker between said transmission of pulses of ultrasound and after a predetermined period following termination of said transmission of a pulse.

2. A detector according to claim 1, further comprising a pitch shifter to adjust the frequency or phase of the detected received signal before it is output by the loudspeaker.

3. A detector according to claim 1, further comprising a full wave rectifier for full wave rectifying the signals supplied to the loudspeaker.

4. A detector according to claim 1, further comprising display means to display a digital output, relating to a frequency of a signal received by said ultrasonic receiving circuit.

5. A detector according to claim 1, further comprising a sealed housing and wherein the loudspeaker is covered by an impermeable membrane.

* * * * *